United States Patent [19]

Virnig et al.

[11] Patent Number: 4,647,688
[45] Date of Patent: Mar. 3, 1987

[54] SUBSTITUTED FATTY ETHERS

[75] Inventors: Michael J. Virnig, Fridley; James P. Clark, St. Anthony; Kenneth D. MacKay, Plymouth, all of Minn.

[73] Assignee: Henkel Corporation, Minneapolis, Minn.

[21] Appl. No.: 706,703

[22] Filed: Feb. 28, 1985

[51] Int. Cl.$^4$ .................. C07C 121/34; C07C 121/16; C07C 103/127; C07C 103/175

[52] U.S. Cl. .................... 558/440; 526/298; 526/304; 526/315; 526/320; 558/441; 558/442; 558/444; 558/447; 560/177; 560/179; 560/183; 560/185; 560/186; 560/205; 560/222; 564/199; 564/201; 568/496; 568/497; 568/678; 568/680

[58] Field of Search ........................ 260/465.6, 465.4; 558/440, 441, 442, 444, 447; 560/222; 564/199, 201

[56] References Cited

U.S. PATENT DOCUMENTS

| | | | |
|---|---|---|---|
| 2,669,558 | 2/1954 | Mowry et al. | 260/465.6 X |
| 2,813,877 | 11/1957 | Lambrech | 260/465.6 X |
| 3,119,848 | 1/1964 | Wrigley et al. | 260/465.6 X |
| 3,799,986 | 3/1974 | Poppelsdorf | 260/465.6 X |
| 4,028,395 | 6/1977 | Prevedello et al. | 260/465.6 X |
| 4,077,916 | 3/1978 | Kulka et al. | 260/465.6 X |
| 4,115,326 | 9/1978 | Plattier et al. | 260/465.6 X |
| 4,216,343 | 8/1980 | Rogier | 568/853 |
| 4,243,818 | 1/1981 | Rogier | 560/224 |
| 4,356,128 | 10/1982 | Rogier | 260/465.6 |

FOREIGN PATENT DOCUMENTS 674307  11/1963  Canada .............. 260/465.6

*Primary Examiner*—Joseph Paul Brust
*Attorney, Agent, or Firm*—Ernest G. Szoke; Patrick J. Span; John Daniel Wood

[57] ABSTRACT

Fatty ethers are provided which are lower alkyl ethers cyano-substituted lower alkyl ethers, ester ethers or amide ethers of fatty alcohols substituted with at least one of the following substituents: formyl, methylol, or acryloxymethyl. The substituted fatty ethers are useful as monomers in a wide variety of polymer systems.

13 Claims, No Drawings

SUBSTITUTED FATTY ETHERS

FIELD OF THE INVENTION

This invention relates to substituted fatty ether compounds. More particularly, this invention relates to substituted fatty alkyl ethers, and their precursors, which are useful as monomers in a wide variety of polymer systems.

BACKGROUND OF THE INVENTION

U.S. Pat. No. 4,356,128 to Rogier discloses that hydroxymethyl fatty nitriles, hydroxymethyl fatty amides, and hydroxymethyl fatty esters are useful as polyols for preparing polyurethane coatings and paints.

U.S. Pat. No. 4,216,343 to Rogier descibes the preparation of hydroxymethyl fatty alcohols and the use thereof with polyisocyanates to form polyurethanes.

U.S. Pat. No. 4,243,818 to Rogier discloses acrylate esters of gem-bis(hydroxymethyl) fatty alcohols and hydroxymethyl fatty alcohols and the use thereof in the preparation of radiation curable coatings.

SUMMARY OF THE INVENTION

This invention relates to compounds having the structural formula:

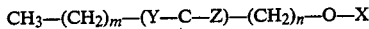

$$CH_3-(CH_2)_m-(Y-C-Z)-(CH_2)_n-O-X$$

wherein:
X is:
(a) lower alkyl;
(b) cyano-substituted lower alkyl;
(c) $-R^1-C(O)-OR^2$; or
(d) $R^3-C(O)-NR^4R^5$;
$R^1$ and $R^3$ are independently lower alkylene;
$R^2$, $R^4$ and $R^5$ are independently lower alkyl;
Y is a formyl, methylol, or acryloxymethyl group;
Z is a hydrogen, methylol or acryloxymethyl group;
provided that Z is hydrogen when Y is formyl;
and m and n are integers, provided that n is greater than 4 and the sum of m and n ranges from 8 to 20.

The preferred compounds are those wherein X is methyl or cyanoethyl, Y is acryloxymethyl, Z is hydrogen, and m is 7 or 8 and n is 8 or 9 provided that the sum of m and n is 16.

As used herein, the term "lower alkyl" refers to groups having from 1 to about 4 aliphatic carbon atoms. As also used herein, the term "acryloxymethyl" refers to groups having the structural formula:

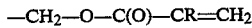

$$-CH_2-O-C(O)-CR=CH_2$$

wherein R is hydrogen or methyl, i.e. compounds containing these groups are acrylic or methacrylic acid esters.

This invention also relates to the use of the compounds of this invention to form polymers and to the polymers formed thereby.

DETAILED DESCRIPTION OF THE INVENTION

The following detailed description will describe the preparation and use of (a) the formyl substituted fatty ether of this invention which is a precursor to the other fatty ethers of this invention; (b) the hydroxyl-substituted fatty ethers of this invention which are useful as polyols and/or as precursors in the preparation of the acryloxymethyl fatty ethers of this invention; and (c) the acryloxymethyl ethers of this invention and their use in curable coatings.

A. Formyl-Substituted Fatty Ethers

The formyl-substituted fatty ethers of this invention are ultimately derived from unsaturated fatty alcohols. The unsaturated fatty alcohols are etherified with an etherifying agent corresponding with the desired structure of X in the formula above. Suitable etherifying agents are lower alkyl halides, cyano-substituted lower alkyl halides, unsaturated nitriles, halo-substituted esters, unsaturated esters, halo-substituted amides, and unsaturated amides.

For example, an unsaturated fatty alcohol can be reacted with a lower alkyl halide in the Williamson ether synthesis of a lower alkyl unsaturated fatty ether. Similarly, a halo-substituted nitrile can be used in the Williamson ether synthesis to prepare a cyano-substituted lower alkyl ether. Another example is the reaction of acrylonitrile with an unsaturated fatty alcohol to prepare a 2-cyanoethyl unsaturated fatty ether.

Other examples are the reaction of methyl chloroacetate or an N,N-dimethyl chloroacetamide with an unsaturated fatty alcohol to prepare compounds wherein $R^1$ and $R^3$ are methylene and $R^2$, $R^4$ and $R^5$ are methyl, respectively. The reaction of methyl acrylate or N,N-dimethyl acrylamide with an unsaturated fatty ether will produce corresponding compounds wherein $R^1$ and $R^3$ are ethylene rather than methylene.

The unsaturated fatty ethers described above can then be reacted with carbon monoxide and hydrogen in the presence of a rhodium catalyst to produce a formyl substituted fatty ether. The conditions under which the formylation reaction is conducted are more particularly described in U.S. Pat. No. 4,356,128 to Rogier, which is incorporated herein by reference thereto.

For example, methyl oleyl ether can be reacted with carbon monoxide and hydrogen in the presence of a rhodium catalyst to produce a methyl 9(10)-formyloctadecanyl ether.

B. Hydroxyl-Substituted Fatty Ethers

The formyl-substituted fatty ether of this invention can be used to prepare hydroxyl-substituted fatty ethers by either of three synthetic routes.

1. Simple Reduction of the Formyl-Substituted Fatty Ether

The formyl-substituted fatty ether can be simply reduced, e.g. with sodium borohydride, to produce a monohydroxymethyl substituted fatty ether, i.e. a compound wherein Z is hydrogen and Y is methylol. The reduction of the formyl-substituted compound with a reagent such as sodium borohydride is within the skill of one of ordinary skill in the art as disclosed in U.S. Pat. No. 4,356,128.

2. Tollens' Reaction of the Formyl-Substituted Fatty Ether

The formyl-substituted fatty ether can be reacted with formaldehyde in the presence of base via a Tollens' reaction to prepare a gem-bis(hydroxymethyl) fatty ether, i.e. a compound wherein both Y and Z are methylol groups. The Tollens' reaction may be conducted as described in U.S. Pat. No. 4,356,128.

3. Uses of Hydroxyl-Substituted Fatty Ethers

The hydroxyl-substitited fatty ethers of this invention are alkanols and polyols which may be reacted in a variety of polymer systems to form useful novel polymers.

For example, the polyols of this invention, e.g. 9,9(10,10)-bis(hydroxymethyl)octadecanyl ethers can be copolymerized with a polyfunctional organic compounds that are copolymerizable with a polyol, e.g. polybasic acids, preferably dibasic acids, polyisocyanates, preferably diisocyanates, etc., to form a variety of novel copolymers, e.g. polyesters, polyurethanes, etc., useful in a variety of applications.

The polyols can also be used to initiate the polymerization of an alkylene oxide to form novel polyethers. When the alkylene oxide chosen is ethylene oxide, the polyether will have both hydrophilic and hydrophobic portions and will thereby have surfactant characteristics.

The monohydroxyl-fatty ethers of this invention can also be reacted with alkylene oxides to form novel polyethers. For example, 9(10)-hydroxymethyloctadecanyl cyanoethyl ether can be reacted with ethylene oxide to prepare a novel polyether adduct having a hydrophilic chain and a long hydrophobic chain with a polar substituent which is useful as a surfactant.

The monohydroxyl-fatty ethers that also contain an acryloxymethyl substituent, e.g. a 9(10)-hydroxymethyl-9(10)-acryloxymethyloctadecanyl ether, can also be used to terminate polymers derived from the polymerization of polyols with polyfunctional organic compounds copolymerizable therewith, e.g. polybasic acids or polyisocyanates, to obtain acryloxymethyl terminated copolymers e.g. polyesters and polyurethanes, that can be cured to form a crosslinked copolymer. These copolymers are especially useful when cured on a substrate to form a crosslinked coating. For example, a 9(10)-hydroxymethyl-9(10)-acryloxymethyloctadecanyl ether can be added to a mixture comprised of a polyol, a polyisocyanate, and a urethane catalyst to form an acryloxymethyl terminated polyurethane that can be radiation cured on a substrate to form a crosslinked polyurethane coating.

C. Acryloxymethyl-Substituted Fatty Ethers

The hydroxymethyl-substituted fatty ethers of this invention can be reacted with an acryloyl compound to prepare the acryloxymethyl substituted fatty ethers of this invention.

The acryloxymethyl fatty ethers of this invention are prepared by reacting the corresponding hydroxymethyl fatty ether with an acryloyl compound that is capable of esterifying the respective hydroxymethyl compound. The hydroxymethyl fatty compounds have the general formula:

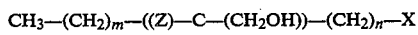

$$CH_3-(CH_2)_m-((Z)-C-(CH_2OH))-(CH_2)_n-X$$

wherein m, n, X and Z are as previously defined. Methods of obtaining these hydroxymethyl fatty compounds are discussed below.

The acryloyl compounds used to esterify the hydroxymethyl fatty compound is preferably an acryloyl halide, such as acryloyl chloride, but may be other reactive acryloyl compounds, such as acryloyl anhydride, acrylic acid or lower alkyl esters thereof.

The amount of acryloyl compound used to esterify the hydroxymethyl fatty polyol will depend, in part, on the nature of the hydroxymethyl fatty polyol and the product desired. When a di-acryloxymethyl compound of this invention is desired, i.e. a compound wherein Y is acryloxymethyl, an amount of the acryloyl compound in excess of 2 equivalents thereof should be used to ensure the full acrylation of the starting gem-bis(hydroxymethyl) fatty compound. When a nonhydroxyl-containing mono-acryloxymethyl compound of this invention is desired, i.e. a compound wherein Y is hydrogen, an amount of the acryloyl compound in excess of 1 equivalent thereof should be used to ensure the full acrylation of the starting hydroxymethyl fatty compound.

When a hydroxymethyl acryloxymethyl fatty compound of this invention is desired, i.e. a compound wherein Y is methylol, a single equivalent of the acryloyl compound should be used in conjunction with techniques to control the reaction to conditions to ensure completion of the reaction. For example, when the acryloyl compound is acrylic acid, it is convenient to remove the water that is a by-product of the acrylation reaction by techniques such as azeotropic distillation and thereby force the reaction to completion.

The acryloxymethyl fatty ethers of this invention are useful as monomers in the preparation of curable polymeric coatings. The compounds of this invention can be homopolymerized or the compounds can be mixed with other ethylenically unsaturated monomers to form a composition of comonomers which can then be polymerized. A composition of this invention is applied to a substrate such as wood, metal, paper, or plastics by any convenient method such as knife, blade, brush, or spray. The coated surface can then be exposed to radiation to cure the composition through the radiation sensitive pi bonds. The coating is cured by the addition polymerization of the components of the composition. Suitable sources of ionizing radiation include ultraviolet light or radioactive sources such as are described in U.S. Pat. No. 3,935,330 to Smith et al.

The coating can also be cured by including in the coating composition free radical initiators such as benzoin ethers, and Michler's Ketone. Other suitable free radical initiators are organic peroxides, hydroperoxides, per acids, per esters, azo compounds, ditertiary butyl peroxide, benzoyl peroxide, 2,4-dichlorobenzoyl peroxide, tertiary butyl hydroperoxide, 2,5-dimethyl-2,5-bis(-hydroperoxy)-hexane, peracetic acid, perbenzoic acid, tertiary butyl peroxypivalate, tertiary butyl peracetic acid and azo-bis-isobutyl nitrile. The free radical initiator may be present at from 0.01 to about 20% by weight of the radiation curable components.

To ensure that the composition does not polymerize prior to the application of the composition to a substrate, a free radical inhibitor may be added to the composition. Examples of suitable inhibitors include hydroquinone and the methyl ether thereof or butylated hydroxy toluene at a level of from about 5 ppm to about 2000 ppm by weight of the radiation curable components.

The amount of radiation necessary to cure the composition will of course depend upon the wavelength and intensity of the radiation, the angle of exposure to the radiation, the thickness of the coating to be applied, and the amount of acryloxymethyl fatty compound in the coating composition as well as the presence or absence of a free radical initiating catalyst. For any given composition, experimentation to determine the amount of radiation sensitive pi bonds not cured following exposure to the radiation source is the best method of determining the amount and duration of the radiation required.

The coatings produced by the cure of the acryloxymethyl fatty compounds of this invention are useful in a wide variety of applications i.e. decorative, maintenance, or industrial coatings. For example, they can be used as binders in inks. In the electronics area, these materials have applications as non-conductive coatings, e.g. solder masks or circuit boards or moisture resistance coatings for curcuit boards and optical fibers.

The use of the acryloxymethyl fatty compounds of this invention should provide excellent flexibility in the final coating and offer good compatibility with other compounds in the coating formulation. The presence of the polar ether and/or nitrile functionality will also lead to improved surface wetting properties as compared with most commercially available curable coatings resulting in better adhesion to the substrate and improved pigment compatibility.

EXAMPLES

The following examples illustrate the preparation of representative substituted fatty ethers of this invention. Examples 1-3 illustrate the preparation of methyl octadecanyl ethers, and Examples 4-6 illustrate the preparation of 2-cyanoethyl octadecanyl ethers.

EXAMPLE 1

PREPARATION OF METHYL 9(10)-FORMYLOCTADECANYL ETHER

| Materials | CHARGE M.W. | Weight (g) | Moles |
| --- | --- | --- | --- |
| Oleyl Methyl Ether | 284 | 438 | 1.54 |
| Trilaurylphosphite | 586 | 2.2 | 0.004 |
| Dicarbonylrhodium (I) 2,4-pentanedionate | 259 | 0.11 | 0.0004 |

EQUIPMENT

A one liter autoclave.

PROCEDURE

The starting ether was degassed by stirring under vacuum. The catalyst and ligand were dissolved in the ether. The mixture was then charged to the autoclave and the system was purged with nitrogen. The system was then heated to 130° C. and pressurized with a hydrogen-carbon monoxide (1:1) mixture. The pressure was maintained at 500–900 psig. After hydrogen-carbon monoxide uptake stopped, the reactor was cooled and the contents discharged into a nitrogen blanketed receiver. The separate runs yielded 443.7 g and 471.8 g of crude product, each.

The crude products were combined and purified by distillation in a wiped-film evaporator. A 9% forecut was removed and then a 73% heartcut was taken to give 668 g of a water white oil. Comparisons of the starting material and product via GLC and IR spectroscopy were consistent with the formation of methyl 9(10)-formyloctadecanyl ether.

EXAMPLE 2

PREPARATION OF METHYL 9(10)-HYDROXYMETHYLOCTADECANYL ETHER

| Materials | CHARGE M.W. | Weight (g) | Moles |
| --- | --- | --- | --- |
| Methyl 9(10)-Formyloctadecanyl Ether | 312 | 334 | 1.07 |
| Nickel Catalyst (Ni-5132P, Harshaw Chemical) | — | 6.6 | — |

EQUIPMENT

A one liter autoclave.

PROCEDURE

The aldehyde and catalyst were charged to the autoclave. The system was purged with nitrogen, pressurized to 600 psig with hydrogen and heated to 190° C. The pressure was maintained between 300 and 550 psig hydrogen. After hydrogen uptake ceased, the autoclave was cooled and the product discharged through a filter press fitted with a 2 micron filter pad to yield 314 g of a slightly viscous light yellow oil. Comparisons of the starting material and product via GLC and IR spectroscopy were consistent with the formation of methyl 9(10)-hydroxymethyloctadecanyl ether.

EXAMPLE 3

PREPARATION OF METHYL 9(10)-(ACRYLOXYLOXYMETHYL)OCTADECANYL ETHER

| Materials | CHARGE M.W. | Weight (g) | Moles |
| --- | --- | --- | --- |
| Methyl 9(10)-(hydroxymethyl)octadecanyl ether | 314 | 150 | 0.48 |
| Acrylic Acid | 72 | 38 | 0.53 |
| p-Toluenesulfonic Acid | 190 | 4.5 | 0.02 |
| Hydroquinone | 110 | 6.0 | 0.05 |
| Dichloromethane | 100 | 68.4 | 0.68 |

EQUIPMENT

A 500 ml three neck round bottom flask was fitted with a magnetic stirrer, Dean-Stark trap for azeotropic water removal, vacuum regulator, and thermometer. It was also fitted with a capillary such that a small stream of air was continuously introduced beneath the surface of the liquid during the reaction.

PROCEDURE

Materials were placed in the flask, the pressure was adjusted to 400 mm of mercury and the reaction heated to reflux. After 3.5 hours, the theoretical amount of water was collected. The reaction mixture was then transferred to a separatory funnel containing 200 ml of toluene and 250 ml of deionized water. The phases were separated and the organic phase was washed twice with 250 ml portions of 2% sodium hydroxide in 30% aqueous methanol, four times with 250 ml portions of 30% aqueous methanol, and then with 250 ml of deionized water. The solvent was removed in vacuo to give 172 g of a pale yellow oil. That the oil contained the desired product was confirmed by NMR and IR spectroscopy.

EXAMPLE 4

PREPARATION OF 2-CYANOETHYL 9(10)-FORMYLOCTADECANYL ETHER

| Materials | CHARGE M.W. | Weight (g) | Moles |
|---|---|---|---|
| Oleyl 2-cyanoethyl ether | 321 | 467 | 1.45 |
| Trilaurylphosphite | 586 | 2.3 | 0.004 |
| Dicarbonylrhodium (I) 2,4-pentanedionate | 259 | 0.117 | 0.00045 |

EQUIPMENT

A one liter autoclave.

PROCEDURE

The ether was thoroughly degassed, then the catalyst and liquid were dissolved in the ether. The resultant reaction mixture was charged to the autoclave, which was then thoroughly purged with nitrogen. The autoclave was pressurized to 900 psig with a hydrogen-carbon monoxide (1:1) mixture and heated to 130° C. The hydrogen-carbon monoxide pressure was maintained between 700 and 110 psig. After gas uptake ceased, the autoclave was cooled and the crude product discharged into a nitrogen blanketed receiver. Two separate runs yielded 506.5 g and 507.7 g of crude product, each.

The crude products were combined and purified by wiped-film evaporator distillation to give 928.2 g of a water white oil. That the oil contained the desired product was confirmed by IR and NMR spectroscopy.

EXAMPLE 5

PREPARATION OF 2-CYANOETHYL 9(10)-HYDROXYMETHYLOCTADECANYL ETHER

| Materials | CHARGE M.W. | Weight (g) | Moles |
|---|---|---|---|
| 2-cyanoethyl 9(10)-formyloctadecanyl ether | 349 | 370 | 1.06 |
| Sodium borohydride | 37.8 | 10.6 | 0.28 |
| Isopropyl alcohol | 60 | 580.9 | 9.68 |

EQUIPMENT

A two liter 3 neck round bottom flask fitted with a stirrer, thermometer, and addition funnel.

PROCEDURE

The sodium borohydride and 290 g of isopropyl alcohol were placed in the flask. The aldehyde was dissolved in the remainder of the isopropyl alcohol and then added over a period of one hour to the borohydride solution. The reaction temperature was maintained at 25° C. during the addition. After addition was complete, the reaction mixture was stirred at 25° C. for 1.5 hours. The reaction mixture was then poured into a separatory funnel containing 2 liter of water, 2 liter of toluene, and 70 g of acetic acid. The resultant mixture was thoroughly shaken and the aqueous phase separated. The organic phase was then washed four times with 1 liter portions of deionized water and then the solvent was removed in vacuo to yield 368 g of an oil.

The identity of the oil was confirmed by IR and NMR analysis.

EXAMPLE 6

PREPARATION OF 2-CYANOETHYL 9(10)-ACRYLOXYMETHYLOCTADECANYL ETHER

| Materials | CHARGE M.W. | Weight (g) | Moles |
|---|---|---|---|
| 2-Cyanoethyl 9(10)-hydroxymethyloctadecanyl ether | 353 | 150 | 0.43 |
| Acrylic Acid | 72 | 91.8 | 1.28 |
| p-Toluenesulfonic Acid | 190 | 4.5 | 0.024 |
| Hydroquinone | 110 | 6.0 | 0.055 |
| Heptane | 100 | 102.6 | 1.02 |

EQUIPMENT

A 500 ml 3 neck flask fitted with a magnetic stirrer, Dean-Stark trap for azeotropic water removal, vacuum regulator and thermometer. It was also fitted with a capillary such that a small stream of air was continuously introduced beneath the surface of the liquid during the reaction.

PROCEDURE

The materials were placed in the flask, the pressure was adjusted to 400 mm of mercury and the reaction heated to reflux. After 6.5 hours, the reaction appeared to be complete based on GLC analysis. The reaction mixture was then transferred to a separatory funnel containing 500 ml of heptane and 500 ml of water. The phases were separated. The organic phase was then washed twice with 500 ml of 1% sodium hydroxide in 30% aqueous methanol, twice with 500 ml of 30% aqueous methanol, and then twice with 500 ml of deionized water. The solvent was removed in vacuo to yield 172 g of an oil. That the oil continued the desired product was confirmed by IR and NMR spectroscopy.

What is claimed is:

1. A compound having the structural formula:

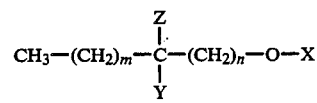

wherein X is a cyano-substituted lower alkyl group; or $$-R^3-C(O)-NR^4R^5,$$

where $R^3$ is lower alkylene and $R^4$ and $R^5$ are independently lower alkyl; Y is a formyl, methylol or $-CH_2-O-C(O)-CR=CH_2$ group where R is hydrogen or methyl; Z is a hydrogen, methylol or $-CH_2-O-C(O)-CR=CH_2$ group where R is hydrogen or methyl and provided that Z is hydrogen when Y is formyl; and m and n are integers provided n is greater than 4 and the sum of m and n ranges from 8 to 20.

2. A compound in accordance with claim 1 wherein X is a 2-cyanoethyl group.

3. A compound in accordance with claim 1 wherein $R^3$ is methylene or ethylene and $R^4$ and $R^5$ are methyl.

4. A compound in accordance with claim 1 wherein at least one of Y and Z is $-CH_2-O-C(O)-CH=CH_2$.

5. A compound in accordance with claim 4 wherein Z is hydrogen.

6. A compound in accordance with claim 4 wherein both Y and Z are —CH$_2$—O—C(O)—CH=CH$_2$.

7. A compound in accordance with claim 4 wherein Z is methylol.

8. A compound in accordance with claim 1 wherein at least one of Y and Z is a methylol group.

9. A compound in accordance with claim 8 wherein both Y and Z are methylol groups.

10. A compound in accordance with claim 8 wherein Z is hydrogen.

11. A compound in accordance with claim 1 wherein Y is formyl and Z is hydrogen.

12. A compound in accordance with claim 1 wherein n is 8 or greater.

13. A compound in accordance with claim 12 wherein m is 7 or 8 and n is 8 or 9 and the sum of m and n is 16.

* * * * *